United States Patent
Satyanarayana et al.

(10) Patent No.: US 7,781,585 B2
(45) Date of Patent: Aug. 24, 2010

(54) CRYSTALLINE FORMS OF GATIFLOXACIN

(75) Inventors: Chava Satyanarayana, Secunderabad (IN); Gorantla Seeta Ramanjaneyulu, Secunderabad (IN); Indukuri Venkata Sunil Kumar, Hyderabad (IN)

(73) Assignee: Matrix Laboratories Ltd (IN)

( * ) Notice: Subject to any disclaimer, the term of this patent is extended or adjusted under 35 U.S.C. 154(b) by 487 days.

(21) Appl. No.: 11/794,276

(22) PCT Filed: May 25, 2005

(86) PCT No.: PCT/IN2005/000166

§ 371 (c)(1),
(2), (4) Date: Dec. 17, 2007

(87) PCT Pub. No.: WO2005/118546

PCT Pub. Date: Dec. 15, 2005

(65) Prior Publication Data

US 2008/0119652 A1  May 22, 2008

(30) Foreign Application Priority Data

Jun. 4, 2004 (IN) .......................... 521/CHE/2004
Jun. 4, 2004 (IN) .......................... 522/CHE/2004
Jun. 4, 2004 (IN) .......................... 523/CHE/2004

(51) Int. Cl.
*C07D 401/10* (2006.01)

(52) U.S. Cl. .................................................... 544/363
(58) Field of Classification Search .................. 544/363
See application file for complete search history.

(56) References Cited

U.S. PATENT DOCUMENTS

| 4,980,470 A | 12/1990 | Masuzawa et al. |
| 4,997,943 A | 3/1991 | Iwata et al. |
| 5,880,283 A | 3/1999 | Matsumoto et al. |
| 6,413,969 B1 | 7/2002 | Raghavan et al. |

FOREIGN PATENT DOCUMENTS

| EP | 0 464 823 A1 | 1/1992 |
| EP | 0 629 621 A1 | 12/1994 |
| WO | WO-03/086402 A1 | 10/2003 |
| WO | WO-03/094919 A2 | 11/2003 |
| WO | WO-03/105851 A1 | 12/2003 |
| WO | WO-03/105852 A1 | 12/2003 |
| WO | WO-2004/012739 A1 | 2/2004 |

*Primary Examiner*—James O Wilson
*Assistant Examiner*—Ebenezer Sackey
(74) *Attorney, Agent, or Firm*—Lerner, David, Littenberg, Krumholz & Mentlik, LLP (57) ABSTRACT

The present invention relates to a process for purification of novel polymorphic form of Gatifloxacin which comprises dissolving Gatifloxacin in about 15-50 volumes of methanol, removing insolubles if any, adding organic base to the solution, maintaining the solution at temperature of 30° C. to 70° C., for about 20 min to 4 hrs, followed by gradual cooling and maintaining the reaction mass to −10 to 20° C. for about 1-4 hrs, isolation and drying at temperature of about 45° C. to 65° C.

22 Claims, 6 Drawing Sheets

CRYSTALLINE FORMS OF GATIFLOXACIN

The present invention relates to novel crystalline forms of Gatifloxacin and process for preparing the same.

BACKGROUND OF THE INVENTION

Gatifloxacin, chemically 1-Cyclopropyl-6-fluoro-8-methoxy-7-(3-methyl piperazin-1-yl)-4-oxo-1,4-dihydro-3-quinoline carboxylic acid, is represented by the following formula,

GATIFLOXACIN

Gatifloxacin belongs to the class of fluoroquinolones, has potent antibacterial activity, has higher selectivity against bacteria from mammalian cells, which results in excellent selective toxicity and is marketed under brand name "Tequin". Gatifloxacin is preferably administered orally or intravenously and the usual dose is 400 mg once daily.

U.S. Pat. No. 4,980,470 describes the method for preparation of Gatifloxacin hemihydrate by condensation of 1-Cyclopropyl-6,7-fluoro-8-methoxy-1,4-dihydro-3-quinoline carboxylic acid with 2-methylpiperazine in anhydrous DMSO followed by column chromatographic purification and recrystallization from methanol.

European Patent No 464,823 discloses a method for the preparation of Gatifloxacin by condensation of 2-methyl piperazine with (1-Cyclopropyl-6,7-difluoro-8-methoxy-4-oxo-1,4-dihydro-3-quinoline carboxylic acid-$O^3,O^4$)bis(acetate-O)-borate in presence of triethyl amine, acetonitrile followed by hydrolysis of the resulting intermediate [1-Cyclopropyl-6-fluoro-8-methoxy-7-(3-methyl-1-piperazinyl)-4-oxo-1,4-dihydro-3-quinoline carboxylic acid-$O^3,O^4$]bis(acetate-O)-borate with triethyl amine in mixture of ethanol, water and crystallization from ethanol.

U.S. Pat. No. 5,880,283 describes the process for Gatifloxacin sesquihydrate by heating the aqueous suspension of 1-Cyclopropyl-6-fluoro-8-methoxy-7-(3-methyl piperazin-1-yl)-4-oxo-1,4-dihydro-3-quinoline carboxylic acid to 80-90° C. followed by hot filtration at that temperature and drying.

U.S. Pat. No. 4,997,943 discloses the Gatifloxacin hydrochloride salts, describes the process for preparation of Gatifloxacin hydrochloride by reaction of 1-cyclopropyl-6,7-difluoro-8-methoxy-4-oxo-1,4-dihydro-3-quinoline carboxylic acid boron difluoride chelate with 2-methyl piperazine in DMSO, isolating the intermediate 1-Cyclopropyl-7-(3-methylpiperazin-1-yl)-6-fluoro-8-methoxy-4-oxo-1,4-dihydro-3-quinoline carboxylic acid boron difluoride chelate which on treatment with triethylamine in aqueous ethanol followed by isolation of the crystals and treating with hydrochloric acid in ethanol.

U.S. Pat. No. 6,413,969 discloses the several polymorphs or hydrate forms of Gatifloxacin and their X-ray diffraction patterns. The Sesquihydrate, pentahydrate and hexahydrate are crystallized directly from aqueous solutions. Other crystalline forms are crystallized from molten phase or by solid-solid transformations. U.S. Pat. No. 6,413,969 further describes Gatifloxacin pentahydrate as the most physically stable form and discloses the process for preparation of Gatifloxacin pentahydrate by water equilibration of any other crystal form of Gatifloxacin.

PCT Publication No WO 03/086402 discloses two anhydrous crystalline forms, Form-I and Form-II of Gatifloxacin, their X-ray diffraction pattern, DSC and IR spectrums and describes the methods for preparation as by removal of water azeotropically from Gatifloxacin hydrate in aromatic or aliphatic hydrocarbon. It further describes the Gatifloxacin hydrate used is having the moisture content ranging from 2.5 to 50.0%.

PCT Publication No. WO 03/94919 discloses the several crystalline forms of Gatifloxacin, Form-A, B, C, D, E1, F, G, H, J and their X-ray diffraction patterns, TGA, DSC and IR spectrums. This PCT publication further describes the process for the preparation methods for the crystalline forms Form-A to Form-J, Form-Ω and Form-T2RP by slurring/crystallization from iso-propanol (Form-A), n-butanol, ethanol (Form-B), n-butanol (Form-C), methanol (Form-D), aqueous methanol (Form-F, Form-G), toluene (Form-H), n-butanol (Form-I, without drying) and the solvated forms Form-J with isopropanol, methyl ethyl ketone, acetone, n-butanol and THF. The Form-E1 is prepared from the mixture of acetonitrile-water, preparation methods for Form-Ω and Form-T2RP were also disclosed.

PCT Publication No WO 03/105851 discloses Gatifloxacin crystalline forms Form-O, mixture of Form-O Sesquihydrate, Form-V and the methods for making them. The Form-O contains the water content equivalent to trihydrate (11.8%), prepared by crystallization from mixed solvent of ethanol-acetonitrile and is the wet compound. The Form-V having the water content about 1% to 3% is prepared by crystallization and treating the isolated solid with moist gas.

PCT Publication No WO 04/12739 discloses the several crystalline forms of Gatifloxacin, Form-L, Form-M, Form-P, Form-Q, Form-S and Form-T1 along with their preparation methods as follows. The Form-L by recrystallization from methanol:water (90:10), Form-M by slurrying in absolute ethanol, Form-P by recrystallization from ethanol:water (99: 1), Form-Q by recrystallization from acetonitrile:water (98: 2), Form-S by recrystallization of wet Gatifloxacin from acetonitrile followed by slurrying in ethanol resulted the wet compound. After drying this Form-S becomes the Form-T2RP. The dry Gatifloxacin on recrystallization from acetonitrile, followed by slurrying in ethanol and drying under vacuum gives the Form-T1.

Our co-pending Indian patent application No. 603/CHE/2003 discloses the preparation of Gatifloxacin by reaction of ethyl 1-cyclopropyl-6,7-difluoro-8-methoxy-4-oxo-1,4-dihydro-3-quinoline carboxylate with aq. hydrofluoroboricacid followed by Isolation of the intermediate, condensation with 2-methyl piperazine, hydrolysis of the resulted intermediate 1-cyclopropyl-7-(3-methylpiperazin-1-yl)-6-fluoro-8-methoxy-oxo-1,4-dihydro-3-quinoline carboxylic acid boron difluoride chelate with triethyl amine in 20% aqueous ethanol and recrystallization from methanol as Gatifloxacin hemihydrate. The X-ray diffraction pattern, IR spectrum of the obtained Gatifloxacin hemihydrate also disclosed.

Surprisingly it has been observed that when recrystallization of Gatifloxacin is attempted in various solvents, new crystalline forms of Gatifloxacin having the water content about 2-5%, characterized by their unique x-ray diffraction pattern.

SUMMARY OF THE INVENTION

Figure 1:
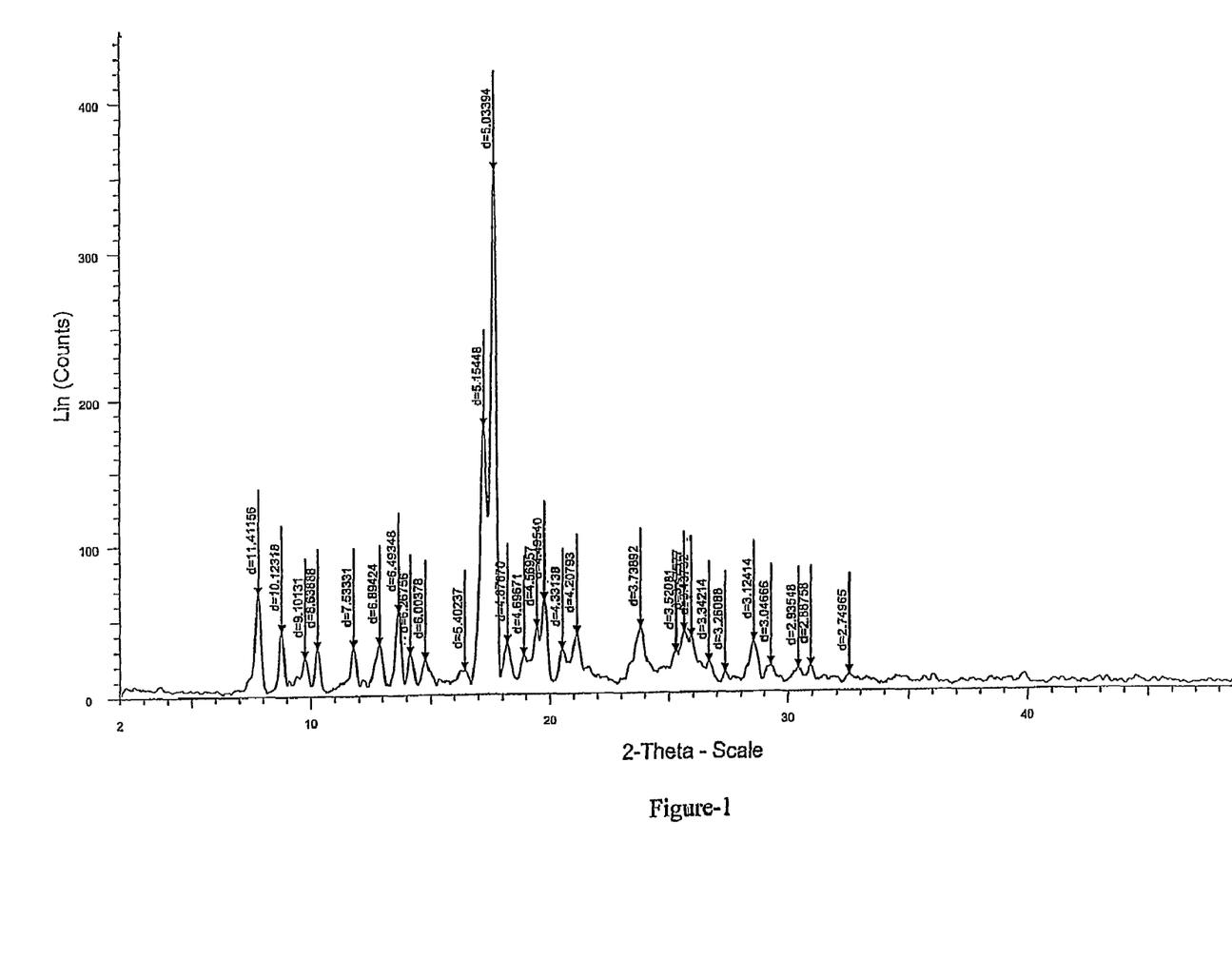
FIG. 1: X-ray diffraction pattern of the crystalline Gatifloxacin Form-X
Figure 2:
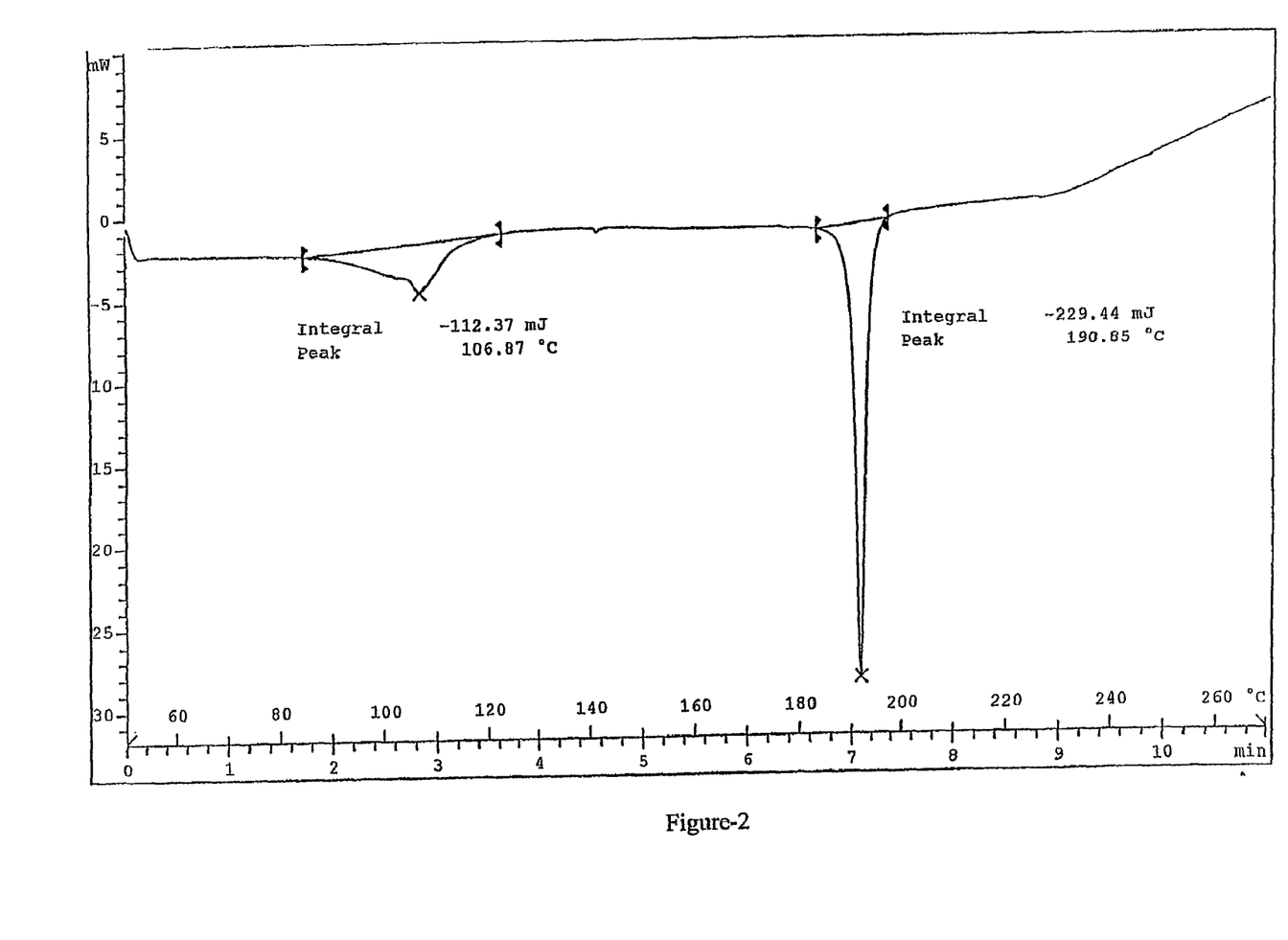
FIG. 2: DSC of the crystalline Gatifloxacin Form-X

According to the present invention there is provided crystalline form-X of Gatifloxacin characterize by the X-ray powder diffraction pattern and DSC expressed in FIG. 1 and FIG. 2

Figure 03:
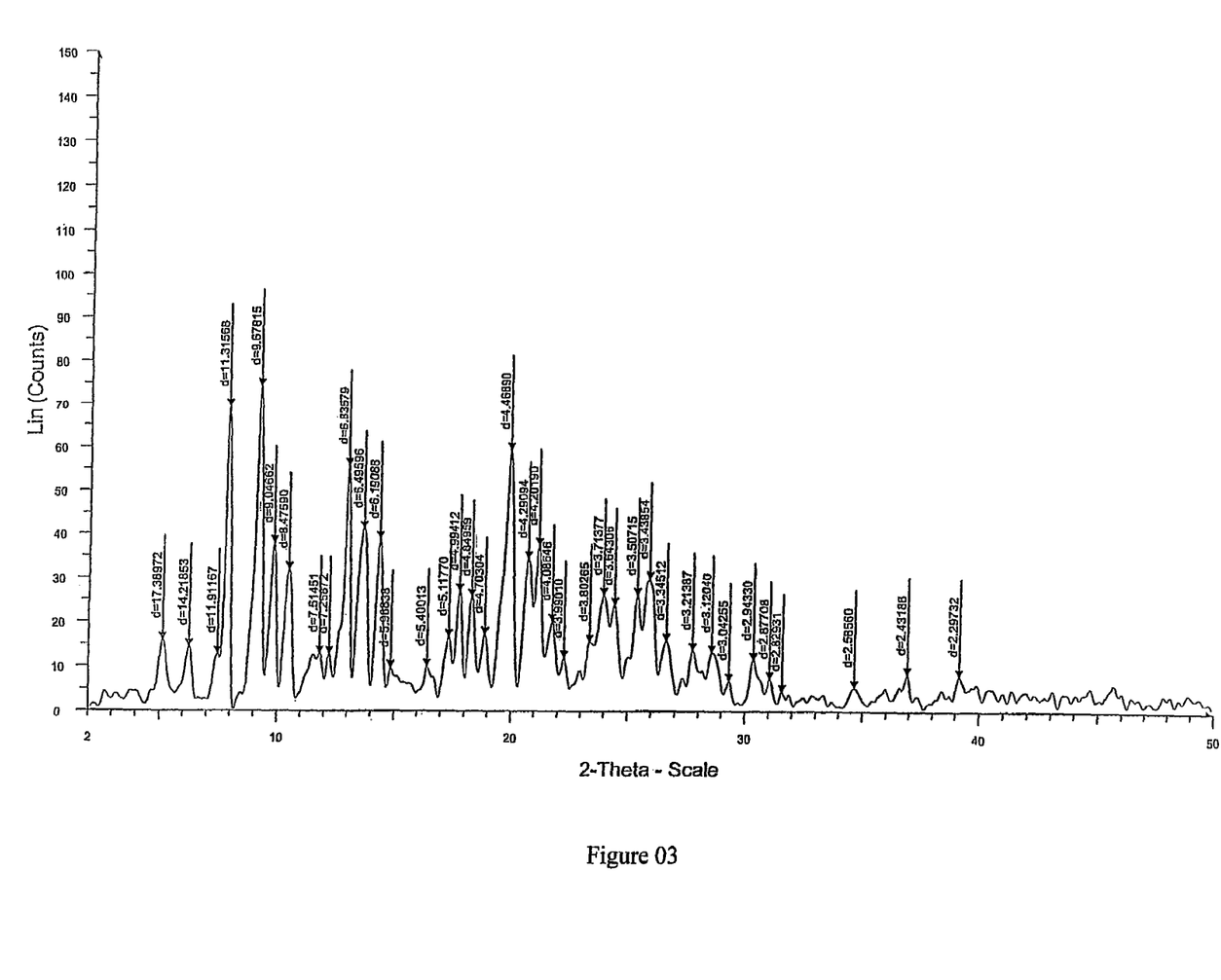
FIG. 3: X-ray diffraction pattern of the crystalline Gatifloxacin Form-Y
Figure 04:
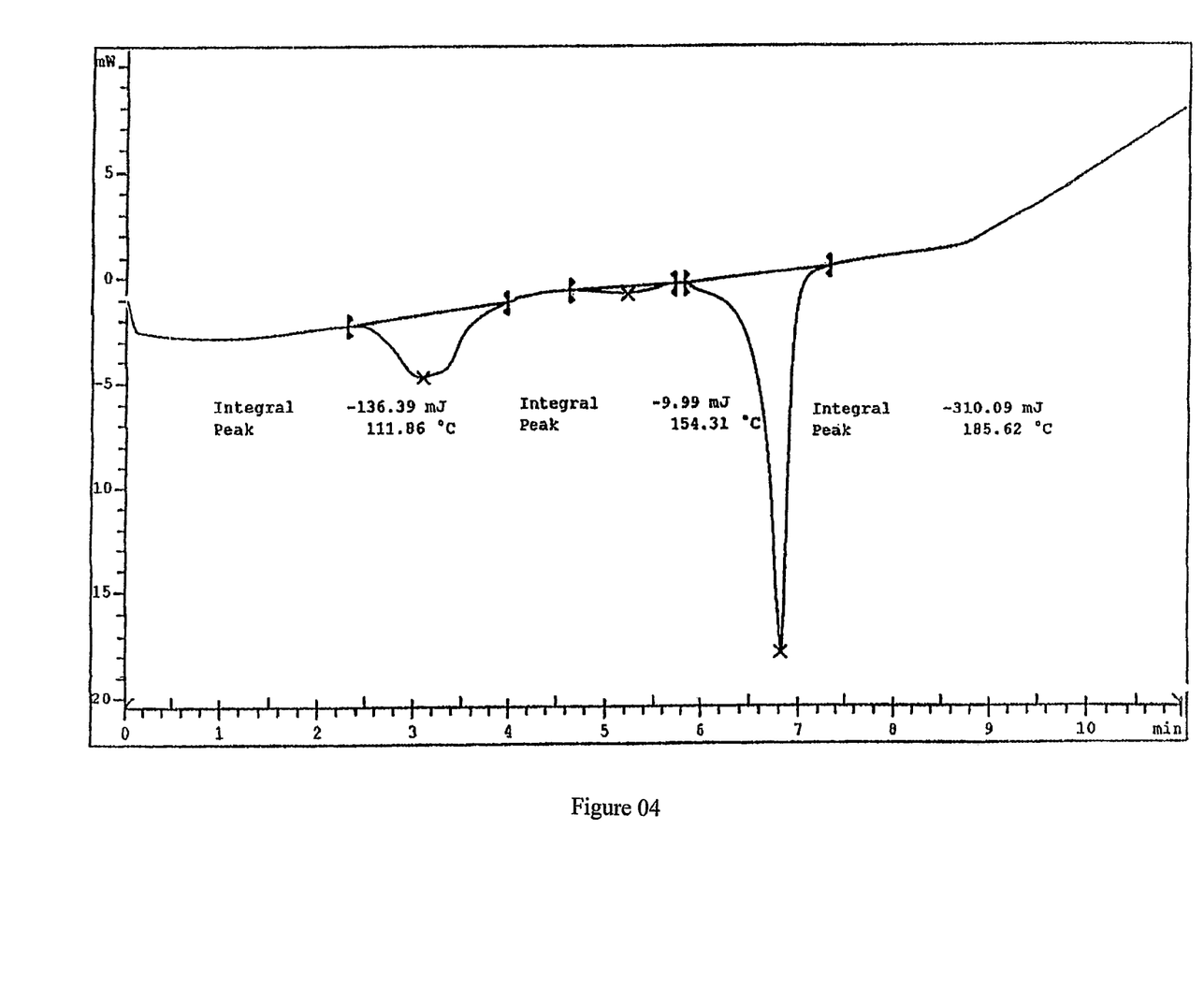
FIG. 4: DSC of the crystalline Gatifloxacin Form-Y

According to a further aspect of the present invention there is provided crystalline form-Y of Gatifloxacin characterizes by the X-ray powder diffraction pattern and DSC expressed in FIG. 3 and FIG. 4

Figure 05:
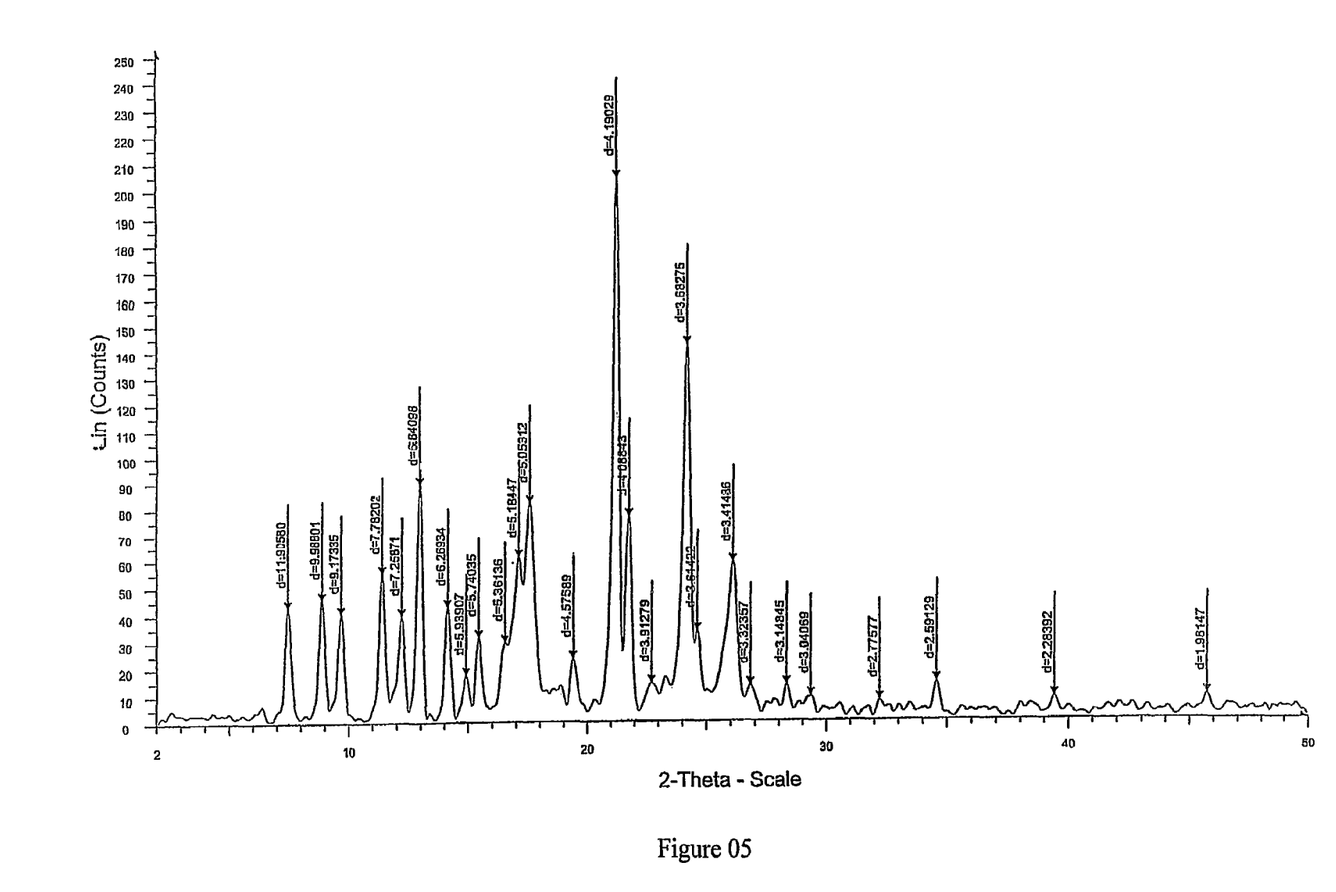
FIG. 5: X-ray diffraction pattern of the crystalline Gatifloxacin Form-Z
Figure 06:
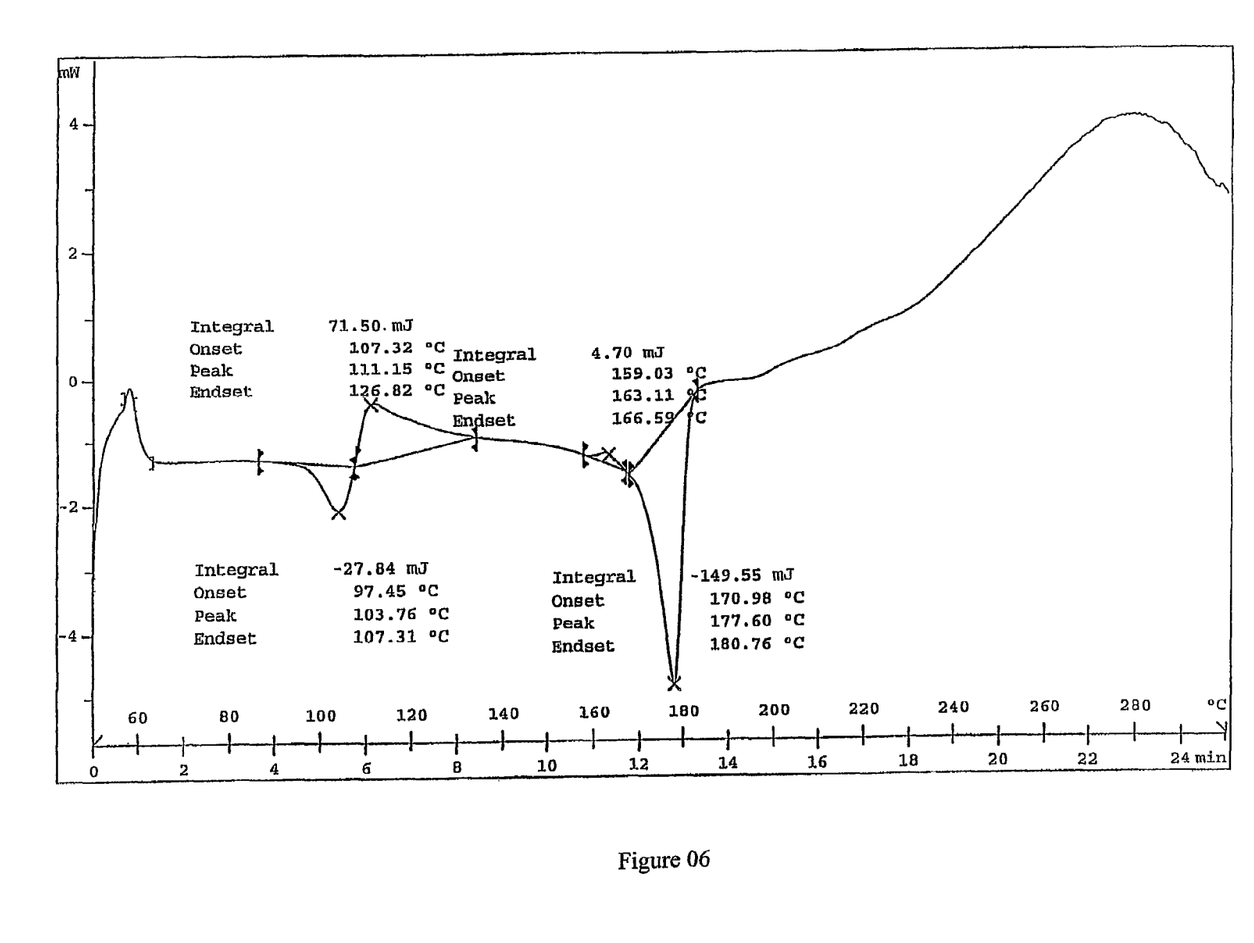
FIG. 6: DSC of the crystalline Gatifloxacin Form-Z

According to a still further aspect of the present invention there is provided crystalline form-Z of Gatifloxacin characterizes by the X-ray powder diffraction pattern and DSC expressed in FIG. 5 and FIG. 6

The present invention also relates to processes for making Gatifloxacin form-X, Y and Z.

DETAILED DESCRIPTION OF THE INVENTION

It has been observed that new crystalline form of Gatifloxacin form-X may be obtained by dissolution in methanol followed by removal of insolubles if any, mixing with organic base, maintaining further for a time period followed by cooling to −10° C. to 20° C., isolating the product and drying to yield Gatifloxacin Form-X.

According to the present invention dissolving Gatifloxacin in about 15-50 volumes preferably about 20-35 volumes of methanol, removing insolubles if any, adding organic base to the solution, the preferred organic base is triethylamine, diisopropyl ethylamine and mixture thereof. Maintaining the solution at temperature of 30° C. to 70° C., preferably at reflux temperature of the solvent for about 20 min. to 4 hrs and more preferably for about 20-60 min, followed by gradual cooling and maintenance of the reaction mass to −10 to 20° C. preferably 0° C. to 10° C. for about 1-4 hrs, isolation and drying at temperature of about 45° C. to 65° C. preferably about 50° C. to 55° C. resulting the Gatifloxacin Form-X. XRD and DSC of the obtained Gatifloxacin Form-X are enclosed as in FIG. 1 and FIG. 2 respectively.

The Gatifloxacin Form-X that results from practicing the invention as exemplified herein can be characterized by its powder X-ray diffraction pattern. FIG. 1 is a representative pattern of Gatifloxacin form-X. The principal peaks observed are at about 7.8, 11.8, 13.7, 17.7, 19.8, 20.6 and 26.0±0.2 2-theta values. The X-ray diffraction further exhibits the peaks at 8.8, 9.8, 10.3, 12.8, 14.2, 14.9, 17.3, 18.2, 19.2, 21.2, 23.9 and 28.6±0.2 2-theta values.

The IR spectrum of Gatifloxacin Form-X produced by the present process is characterized by the following bands: 3408, 1722, 1617, 1555, 1510, 1462, 1392, 1320, 1279, 1058, 939 and 822±2 cm$^{-1}$ along with other absorption peaks.

The Gatifloxacin form-X of the present process is further characterized by the DSC thermogram data, for example, as disclosed in FIG. 2. The DSC thermogram is characterized by a small endotherm at about 107° C. believed to be a solid-solid transformation and a melting peak at 191° C.

The Gatifloxacin Form-X of the present invention further exhibits the water content in the range of 2 to 5%.

Crystalline form of Gatifloxacin form-Y may be obtained by dissolution in methanol by heating followed by removal of insolubles, concentrating the solution to about half of the original volume to one third volume under vacuum followed by gradual cooling and maintenance at about −10° C., isolation and drying gives the Gatifloxacin Form-Y.

According to the present invention dissolving Gatifloxacin in about 15 to 50 volumes preferably about 20 to 35 volumes of methanol by heating to reflux temperature, removing insolubles if any, reducing the volume of the solution to about half of the original volume to one third volume under reduced pressure at temperature below 60° C. preferably below 50° C., gradual cooling and maintaining at temperature of about 10° C. to −20° C. preferably −5° C. to −15° C., for about 30 min. to about 4 hrs, preferably for 30 min., to 2 hrs followed by isolating and drying at temperature of about 45° C. to 65° C. preferably about 50° C.-55° C. yields the Gatifloxacin Form-Y. The XRD and DSC of the obtained Gatifloxacin Form-Y are as per the enclosed FIG. 3 and FIG. 4 respectively.

The Gatifloxacin Form-Y that results from practicing the invention as exemplified herein can be characterized by its powder X-ray diffraction pattern. FIG. 3 is a representative pattern of Gatifloxacin form-Y. The principal peaks observed are at about 5.1, 6.2, 7.8, 9.1, 9.8, 10.4, 12.9, 13.6, 14.3, 17.3, 17.7, 18.3, 18.8, 19.6, 20.7, 21.1, 23.4, 23.9, 24.4, 25.4, 25.9 and 26.6±0.2 2-theta values.

The IR spectrum of Gatifloxacin Form-Y produced by the present process is characterized by the following bands: 3425, 1725, 1618, 1542, 1511, 1461, 1393, 1356, 1320, 1279, 1058, 939 and 822 cm$^{-1}$±2 cm$^{-1}$ along with other absorption peaks.

The Gatifloxacin form-Y of the present process is further characterized by the DSC thermogram data, for example, as disclosed in FIG. 4. The DSC thermogram is characterized by a broad endotherm at about 112° C. believed to be a solid-solid transformation and a melting peak at 186° C.

The Gatifloxacin Form-Y of the present invention is having the water content in the range of 2 to 5%.

Crystalline form of Gatifloxacin form-Z may be obtained by dissolution in methanol by heating followed by removal of insolubles, followed by gradual cooling and maintenance at about 0° C., isolation and drying gives the Gatifloxacin Form-Z.

According to the present invention dissolving Gatifloxacin in about 15 to 50 volumes preferably about 20 to 35 volumes of methanol by heating to reflux temperature, removing insolubles if any, cooling and maintaining the resultant clear solution to a temperature of about 10° C. to −10° C., for about 30 min., to 4 hrs preferably for about 1 to 2 hrs followed by isolating and drying at temperature of about 45 to 65° C. preferably about 50-55° C. gives the Gatifloxacin Form-Z. The obtained Gatifloxacin Form-Z XRD and DSC are as per the enclosed FIG. 5 and FIG. 6 respectively.

The Gatifloxacin Form-Z that results from practicing the invention as exemplified herein can be characterized by its powder X-ray diffraction pattern. FIG. 5 is a representative pattern of Gatifloxacin form-Z. The principal peaks observed are at about 7.3, 8.7, 9.5, 11.2, 12.1, 12.8, 14.0, 14.8, 15.3, 16.0, 19.2, 21.0, 21.6, 23.2, 24.0, 24.4, 25.9 and 26.6±0.2 2-theta values.

The Gatifloxacin form-Z of the present process is further characterized by the DSC thermogram data, for example, as disclosed in FIG. 6. The DSC thermogram is characterized by a small broad endotherm at about 104° C. and a sharp strong endotherm peak at 181° C.

The Gatifloxacin Form-Z of the present invention is having the water content in the range of 2 to 5%.

The stating material Gatifloxacin is prepared by the prior art methods.

The invention can be further illustrated by the below non-limiting examples.

EXAMPLE-1

Preparation of crystalline Gatifloxacin Form-X

Gatifloxacin (25.0 g) is suspended in methanol (625 ml) the temperature is raised and maintained at 60° C. to 65° C. for 20 min to get a clear solution. Activated carbon is added, mixed for 30 min and the solution is filtered. Triethyl amine (6.5 g) is added to the filtrate, maintained at reflux temperature for 45 min. The reaction mixture is gradually cooled and maintained at 8° C. to 10° C. for 2 hrs. The product is filtered, washed with methanol (50 ml) and dried at 45° C. to 50° C. to constant weight.

Dry weight of the pure Gatifloxacin is 18.0 g (Yield: 72.0%)

The X-ray diffraction pattern and DSC is as indicated in FIG. 1 & FIG. 2.

EXAMPLE-2

Preparation of Crystalline Gatifloxacin Form-X

Gatifloxacin (25.0 g) is suspended in methanol (625 ml), temperature is raised and maintained at 60° C. to 65° C. for 20 min to get a clear solution. Activated carbon is added, mixed for 30 min and the solution is filtered. Diisopropyl ethylamine (8.6 g) is added to the filtrate, maintained at reflux temperature for 45 min. The reaction mass is gradually cooled and maintained at 5° C. to 10° C. for 2 hrs. The product is filtered, washed with methanol (50 ml) and dried at 45° C.-50° C. to constant weight.

Dry weight of the pure Gatifloxacin is 17.8 g (Yield: 71.2%)

The X-ray diffraction pattern and DSC is as indicated in FIG. 1 & FIG. 2.

EXAMPLE-3

Preparation of Crystalline Gatifloxacin Form-Y

Gatifloxacin (79.0 g) is suspended in methanol (2765 ml, 35 volumes), the temperature is raised to reflux temperature to get a clear solution, and the solution is filtered in hot. The filtrate is concentrated to about 1200 ml volume under reduced pressure at temperature below 50° C. The reaction mass is gradually cooled and maintained at −10° C. to −8° C. for 45 min. The product is filtered, washed with methanol (40 ml) and dried at 50° C.-55° C. to constant weight.

The dry weight of the Gatifloxacin Form-Y is 60.4 g (yield: 76.5%),

Water content (by KF): 3.11%

The XRD and DSC pattern are as indicated in FIG. 3, and FIG. 4.

EXAMPLE-4

Preparation of Crystalline Gatifloxacin Form-Z

The Gatifloxacin (6.3 g) is suspended in methanol (190 ml, 30 volumes), the temperature is raised and maintained at reflux temperature for 30 min. to get a clear solution. The solution is filtered. The filtrate is gradually cooled and maintained at −2° C. to 0° C. for 1 hr. The product is filtered, washed with methanol (60 ml) and dried at 50° C.-55° C. to constant weight.

The dry weight of the Gatifloxacin is 5.6 g (Yield: 70.0%)

Water content by KF): 2.55%

The XRD and DSC pattern are as indicated in FIG. 5 and FIG. 6.

We claim:

1. A crystalline form of Gatifloxacin (form-X) that exhibits characteristic XRD-peaks expressed in 2θ at 7.8, 8.8, 9.8, 10.3, 11.8, 12.8, 13.7, 14.2, 14.9, 17.3, 17.7, 18.2, 19.2, 19.8, 20.6, 21.2, 23.9, 26.0 and 28.6 ± 0.2 degrees.

2. A crystalline form of Gatifloxacin (form-Y) that exhibits characteristic XRD-peaks expressed in 2θ at 5.1, 6.2, 7.8, 9.1, 9.8, 10.4, 12.9, 13.6, 14.3, 17.3, 17.7, 18.3, 18.8, 19.6, 20.7, 21.1, 23.4, 23.9, 24.4, 25.4, 25.9 and 26.6 ± 0.2 degrees.

3. A crystalline form of Gatifloxacin (form-Z) that exhibits characteristic XRD-peaks expressed in 2θ at 7.3, 8.7, 9.5, 11.2, 12.1, 12.8, 14.0, 14.8, 15.3, 16.0, 19.2, 21.0, 21.6, 23.2, 24.0, 24.4, 25.9 and 26.6 ±0.2 degrees.

4. A process for the preparation of Gatifloxacin Form-X comprising the steps:
dissolving Gatifloxacin in methanol,
removing insolubles if any,
adding an organic base,
maintaining the reaction mixture at an appropriate temperature,
cooling the reaction mixture to −10° C. to 20° C.,
maintaining the reaction mixture at that temperature for 1 hr to 4 hrs,
isolating and drying the product.

5. A process as claimed in claim 4, wherein the volume of methanol for dissolution of Gatifloxacin is 15 to 50 volumes, with respect to Gatifloxacin.

6. A process as claimed in claim 4 or 5, wherein Gatifloxacin is dissolved in methanol at a temperature in between 45° C. and reflux temperature.

7. A process as claimed in claim 4, wherein the addition of the organic base is carried out at a temperature from 30° C. to 70° C.

8. A process as claimed in claim 4, wherein the organic base is triethyl amine or diisopropyl ethylamine.

9. A process as claimed in claim 4, wherein the maintenance temperature of the reaction mass is between 30° C. and 70° C.

10. A process as claimed in claim 4, wherein the drying temperature is between 45° C. and 65° C.

11. A process for the preparation of novel crystalline Gatifloxacin Form-Y comprising the steps:
dissolving Gatifloxacin in methanol,
removing insolubles if any,
concentrating the reaction mass under reduced pressure, cooling the reaction mass to a temperature of −20° C. to 10° C., maintaining the reaction mixture at −20° C. to 10° C. for 30 min to 4 hrs, isolating and drying the product.

12. A process as claimed in claim 11, wherein the volume of methanol for dissolution of Gatifloxacin is 15 to 50 volumes with respect to Gatifloxacin.

13. A process as claimed in claims 11 or 12, wherein Gatifloxacin is dissolved in methanol at a temperature of 45° C. to reflux temperature.

14. A process as claimed in claim 11, wherein the reaction mass is concentrated to one half to one third of the original volume.

15. A process as claimed in claim 11, wherein the drying temperature is between 45° C. and 65° C.

16. A process for the preparation of novel crystalline Gatifloxacin Form-Z comprising the steps:
    dissolving Gatifloxacin in methanol,
    removing insolubles if any,
    cooling the reaction mixture to a temperature of −10° C. to 10° C.,
    maintaining the reaction mixture at −10° C. to 10° C. for 30 min. to 4 hrs,
    isolating and drying the product.

17. A process as claimed in claim 16, wherein the volume of methanol for dissolution of Gatifloxacin is 15 to 50 volumes, with respect to Gatifloxacin.

18. A process as claimed in claim 16, wherein the dissolution of Gatifloxacin in methanol is at a temperature of 30° C. to 70° C.,.

19. A process as claimed in claim 16, wherein the drying temperature is 45° C. to 65° C.

20. A process as claimed in claim 18, wherein dissolution of Gatifloxacin in methanol is at the reflux temperature of the solvent.

21. A process as claimed in any one of claims 5, 12, and 17, wherein the volume of methanol for dissolution of Gatifloxacin is 20 to 35 volumes with respect to Gatifloxacin.

22. A process as claimed in claim 9, wherein the maintenance temperature of the reaction mass is the reflux temperature of the solvent.

* * * * *